United States Patent [19]

Alsop

[11] 3,979,141
[45] Sept. 7, 1976

[54] PRESSURE-SENSITIVE RECORDING SYSTEM COMPRISING 3'-AMINO-6' OR 7'-(PYRAZOL-1-YL)FLUORAN COMPOUNDS AS COLOR PRECURSORS

[75] Inventor: Derek J. Alsop, North Tonawanda, N.Y.

[73] Assignee: Moore Business Forms, Inc., Niagara Falls, N.Y.

[22] Filed: July 9, 1975

[21] Appl. No.: 594,287

Related U.S. Application Data

[62] Division of Ser. No. 525,991, Nov. 21, 1974, Pat. No. 3,929,828.

[52] U.S. Cl. .............................. 282/27.5; 428/323; 428/307
[51] Int. Cl.² .......................................... B41M 5/22
[58] Field of Search ........... 428/307, 323; 282/27.5; 260/310 R

[56] References Cited
UNITED STATES PATENTS

| | | | |
|---|---|---|---|
| 3,669,711 | 6/1972 | Kimura et al. | 428/307 |
| 3,669,712 | 6/1972 | Kimura et al. | 428/307 |
| 3,769,057 | 10/1973 | Lin | 428/307 |
| 3,769,062 | 10/1973 | Ishige et al. | 428/307 |
| 3,930,672 | 1/1976 | Ozutsumi | 282/27.5 |
| 3,947,471 | 3/1976 | Akamatsu et al. | 282/27.5 |

Primary Examiner—Donald B. Moyer

[57] ABSTRACT

Disclosed are normally substantially colorless chromogenic 3'-amino-6' or 7'-(pyrazol-1-yl)fluoran color precursor compounds having the following generic structural formula:

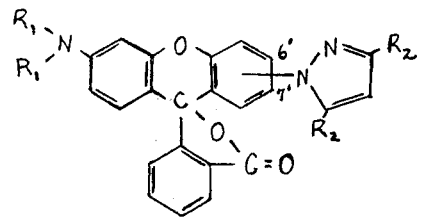

wherein each $R_1$ represents either a hydrogen atom or a lower alkyl group having from one to five carbon atoms; wherein each $R_2$ represents either a hydrogen atom, a substituted or unsubstituted lower alkyl group having from one to five carbon atoms or a substituted or unsubstituted phenyl group; and wherein the pyrazolyl group is attached to the fluoran moiety at either the 6' position or the 7' position of the latter. These compounds are generally substantially colorless but capable of becoming highly colored when brought into reactive contact with many conventional Lewis acid materials. Accordingly, these compounds are highly useful as a component of pressure-sensitive copying papers.

4 Claims, No Drawings

PRESSURE-SENSITIVE RECORDING SYSTEM COMPRISING 3'-AMINO-6' OR 7'-(PYRAZOL-1-YL)FLUORAN COMPOUNDS AS COLOR PRECURSORS

CROSS REFERENCE TO RELATED APPLICATION

This is a divisional of co-pending application Ser. No. 525,991, filed Nov. 21, 1974, now U.S. Pat. No. 3,929,828.

BACKGROUND OF THE INVENTION

1. Field of the Invention

The present invention relates to initially colorless chromogenic, color precursor compounds having particular utility in the field of carbonless copying. These compounds may be utilized, for example, in the production of self-marking impact papers of the transfer or manifolding type wherein a first marking ingredient is carried on one sheet of paper for reaction with a second marking ingredient normally carried on a mating sheet of paper. Specifically the invention relates to a family of chromogenic 3'-amino-6' or 7'-(pyrazol-1-yl)fluoran compounds having the following structural formula:

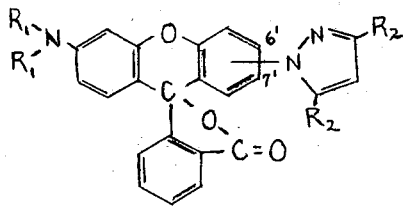

wherein each $R_1$ represents either a hydrogen atom or a lower alkyl group having from one to five carbon atoms; wherein each $R_2$ represents either a hydrogen atom, a substituted or unsubstituted lower alkyl group having from one to five carbon atoms or a substituted or unsubstituted phenyl group; and wherein the pyrazolyl group is attached to the fluoran moiety at either the 6' position or the 7' position of the latter.

2. Description of the Prior Art

Impact or pressure sensitive carbonless transfer papers have recently come into wide usage in the United States and throughout the world. Ordinarily, such papers are printed and collated into manifolded sets capable of producing multiple copies. In this connection, pressure applied to the top sheet causes a corresponding mark on each of the other sheets of the set.

The top sheet of paper, upon which the impact or pressure is immediately applied, ordinarily has its back surface coated with microscopic capsules containing one of the reactive ingredients which produce a mark. A receiver sheet, placed in contact with such back face of the top sheet has its front surface coated with a material having a component reactive with the contents of the capsules so that when capsules are ruptured upon impact by stylus or machine key, the initially colorless or substantially colorless contents of the ruptured capsules react with a coreactant therefor on the receiver sheet and a mark forms on the receiver sheet corresponding to the mark impressed by the stylus or machine key.

In the art, impact transfer papers are designated by the terms CB, CFB and CF, which stand respectively for "coated back", "coated front and back" and "coated front". Thus, the CB sheet is usually the top sheet and the one on which the impact impression is directly made; the CFB sheets are the intermediate sheets, each of which have a mark formed on the front surface thereof and each of which also transmits the contents of ruptured capsules from its back surface to the front of the next succeeding sheet; and the CF sheet is the last sheet and is only coated on its front surface to have an image formed thereon. The CF sheet is not normally coated on its back surface as no further transfer is desired.

While it is customary to coat the capsules on the back surface and to coat the co-reactant for the capsules contents on the front surface of each sheet, this procedure could be reversed if desired. Further, with some systems, coatings need not be used at all and the co-reactive ingredients may be carried in the sheets themselves, or one may be carried in one of the sheets and the other may be carried as a surface coating. Further, the reactants may both comprise microencapsulated liquids. Patents illustrative of many of the various kinds of systems which may incorporate such coreactive ingredients and which may be used in the production of manifolded transfer papers include, for example, U.S. Pat. No. 2,299,694 to Green, U.S. Pat. No. 2,712,507 to Green, U.S. Pat. No. 3,016,308 to Macaulay, U.S. Pat. No. 3,429,827 to Ruus and U.S. Pat. No. 3,720,534 to Macaulay et al.

The most common variety of carbonless impact transfer paper, and the type with which the compounds of the present invention are preferably utilized, is the type illustrated, for example, in Green ('507) and Macaulay ('308) wherein microscopic capsules containing a liquid fill comprising a solution of an initially colorless chemically reactive color forming dye precursor are coated on the back surface of the sheet, and a dry coating of a co-reactant chemical for the dye precursor is coated on the front surface of a receiving sheet.

Many color precursors useful in connection with carbonless copying systems are known to those skilled in the art to which the present invention pertains. For example, specific reference is made to the color precursors mentioned in the patent to Phillips, Jr. et al, U.S. Pat. No. 3,455,721 and particularly to those listed in the paragraph bridging columns 5 and 6 thereof. A variety of fluoran type color precursors are also disclosed in U.S. Pat. No. 3,501,331, U.S. Pat. No. 3,617,335, U.S. Pat. No. 3,669,711, U.S. Pat. No. 3,669,712 and U.S. Pat. No. 3,697,540 to Kimura et al, in U.S. Pat. No. 3,627,787 and U.S. Pat. No. 3,681,390 to Lin and in U.S. Pat. No. 3,725,416 to Yamamoto et al. These materials are capable of reacting with a CF coating containing an acidic material such as the acid-leached bentonite-type clay disclosed in application Ser. No. 125,075 to Baxter filed Mar. 17, 1971 (the entirety of which is hereby specifically incorporated by reference) or the acid-reactant organic polymeric material disclosed in the Phillips, Jr. et al, '721 patent.

Many of the color precursors disclosed in the patents referred to above, are capable of undergoing an acid-base type reaction with an acidic material. Other previously known color precursors are the spiro-dipyran compounds disclosed in the patent to Harbort, U.S. Pat. No. 3,293,060 with specific reference being made to the disclosure of the '060 patent extending from column 11, line 32 through column 12, line 21. The color precursors disclosed in the patents listed above are generally initially colorless and are capable of becoming highly colored when brought into contact with an acidic layer such as an acid-leached bentonite-type clay or an acid-reacting polymeric material, or the like.

Generally speaking, the color precursor materials disclosed above are dissolved in a solvent and the solution is encapsulated in accordance with the procedures and processes described and disclosed by Macaulay ('308) and by Green ('507) as mentioned above. Other processes for encapsulating color precursors are disclosed in U.S. Pat. No. 3,429,827 to Ruus and U.S. Pat. No. 3,578,605 to Baxter. In this connection, it should be mentioned that the exact nature of the capsule itself is not critical as long as the same is capable of containing the color precursor and can be ruptured by the application of pressure in accordance with conventional carbonless copying procedures. Solvents known to be useful in connection with dissolving color precursors include chlorinated biphenyls, vegetable oils (castor oil, coconut oil, cotton seed oil, etc.) esters (dibutyl adipate, dibutyl phthalate, butyl benzyl adipate, benzyl octyl adipate, tricresyl phosphate, trioctyl phosphate, etc.), petroleum derivatives (petroleum spirits, kerosene, mineral oils, etc.), aromatic solvents (benzene, toluene, etc.), silicone oils, or combinations of the foregoing. Particularly useful are the alkylated naphthalene solvents disclosed in U.S. Pat. No. 3,806,463 to Konishi et al.

For a disclosure of acidic coatings which are capable of converting the color precursors into their highly colored form, reference is made to the disclosures of U.S. Pat. No. 3,662,364, U.S. Pat. No. 3,330,722, U.S. Pat. No. 3,389,007 and U.S. Pat. No. 3,293,060, as well as to the disclosure of Baxter application Ser. No. 125,075 referred to above.

In the color forming systems outlined above, as will be appreciated by those skilled in the art, the color precursors are conventionally contained in pressure rupturable microcapsules which are included in the back coatings of the sheets of carbonless copying manifolded sets. Further, it will be appreciated that the acidic coatings are generally utilized as front coatings with the color precursor material in a solvent therefor being transferred from an adjacent back coating to the acidic layer front coating upon rupture of the capsules which contain the color precursor material.

SUMMARY OF THE INVENTION

It is an object of this invention to provide new and improved compounds having chromogenic properties and which may be incorporated in a paper sheet or coated onto the surface thereof to provide a manifolding unit, and which are, moreover, useful in carrying out improved methods of marking involving reactive contact with a color-activating material to yield vividly colored reaction products in areas where marking is desired.

It is another object of this invention to provide chromogenic compounds which are substantially colorless or only slightly colored offering a new and improved variety of chromogenic characteristics and yielding novel vividly colored substances upon contact with color-activating materials.

It is a further object of this invention to provide new and improved, normally substantially colorless, chromogenic substances yielding colored reaction products when placed in reactive contact with Lewis acid materials or the like.

The foregoing objects are achieved by the provision of a family of substantially colorless chromogenic 3'-amino-6' or 7'-(pyrazol-1-yl) fluoran color precursor compounds having the following structural formula:

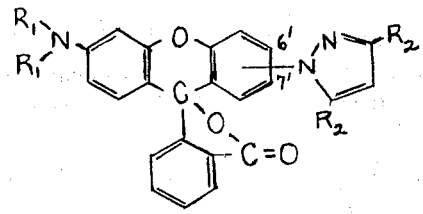

wherein each $R_1$ represents either a hydrogen atom or a lower alkyl group having from one to five carbon atoms; wherein each $R_2$ represents either a hydrogen atom, a substituted or unsubstituted lower alkyl group having from one to five carbon atoms or a substituted or unsubstituted phenyl group; and wherein the pyrazolyl group is attached to the fluoran moiety at either the 6' position or the 7' position of the latter.

DETAILED DESCRIPTION OF THE PREFERRED EMBODIMENTS

The present invention is directed to a family of normally substantially colorless chromogenic 3'-amino-6' or 7'-(pyrazol-1-yl) fluoran color precursor compounds having the following structural formula:

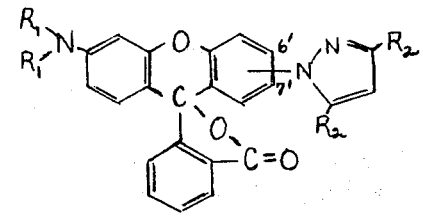

wherein each $R_1$ represents either a hydrogen atom or a lower alkyl group having from one to five carbon atoms; wherein each $R_2$ represents either a hydrogen atom, a substituted or unsubstituted lower alkyl group having from one to five carbon atoms or a substituted or unsubstituted phenyl group; and wherein the pyrazolyl group is attached to the fluoran moiety at either the 6' position or the 7' position of the latter. These compounds are substantially colorless; however, when brought into contact with a solid Lewis acid electron acceptor material such as the acid-leached bentonite-type clay disclosed in the application of Baxter, Ser. No. 125,075, they may be converted into a highly colored form. Various other solid acidic materials which are generally capable of converting these compounds into their highly colored form are disclosed in U.S. Pat. No. 3,622,364, U.S. Pat. No. 3,330,722, U.S. Pat. No. 3,389,007 and U.S. Pat. No. 3,293,060 referred to above.

The fluoran compounds of the present invention may be prepared by reacting one mole of an appropriate o-(4-amino-2-hydroxybenzoyl)benzoic acid with one mole of an appropriately substituted 1-(hydroxyphenyl)pyrazole compound in the presence of a condensing agent such as sulfuric acid, phosphorus pentoxide, polyphosphoric acid or zinc chloride and in accordance with the following formula:

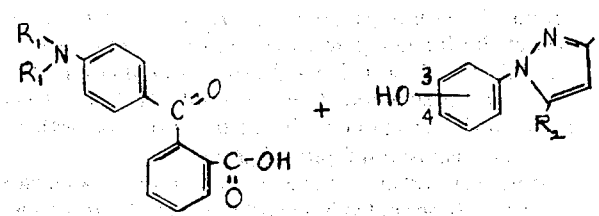

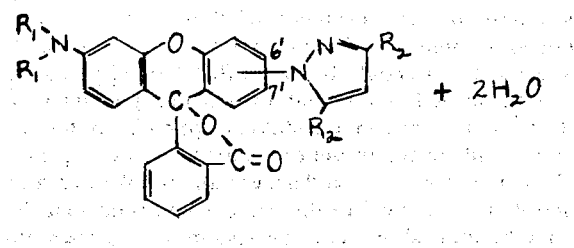

wherein $R_1$ and $R_2$ are as defined above; wherein the hydroxy group is attached to the phenyl group of the pyrazole compound at either the 3 position or 4 position thereof; and wherein in the product compound, the pyrazolyl group is attached to the fluoran moiety at either the 6' position or 7' position of the latter. The substituted 1-(hydroxyphenyl) pyrazole compound may be produced by treating a corresponding 1-(methoxyphenyl)pyrazole compound with HI and the 1-(methoxyphenyl) pyrazole compound may be produced by reacting a methoxy phenyl hydrazine compound with an appropriate diketone in accordance with the following formula:

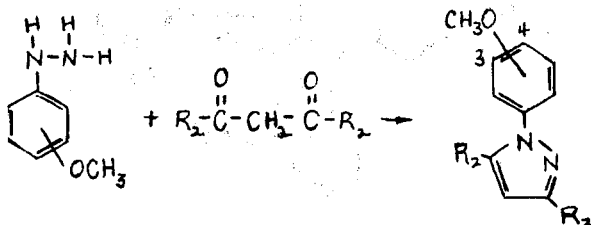

wherein $R_2$ is as defined above and wherein the methoxy group is attached to the phenyl group of the hydrazine compound at either its meta position or its para position. Methoxy phenyl hydrazine compounds may be produced from anisidine by the process disclosed in J. Chem. Soc. (1921) pp 1640–41, the entirety of which disclosure is hereby specifically incorporated by reference.

EXAMPLE I 27.6 gms (0.2 moles) of m-methoxy phenyl hydrazine were admixed at room temperature with 20.0 gms (0.2 moles) of acetyl acetone in a flask. There was an immediate reaction and thereafter the reaction mixture was heated on a steam bath for about an hour to complete the elimination of water from the 3,5-dimethyl-1-(3-methoxyphenyl) pyrazole thus produced.

EXAMPLE II 40 gms of 3,5-dimethyl-1-(3-methoxy phenyl) pyrazole produced in accordance with Example I were added to 125 ml of a constant boiling aqueous solution of HI (approximately 57% HI by weight) and the mixture was refluxed for 12 to 16 hours. The reaction mixture was allowed to cool to room temperature and was then poured into 500 ml of ice water. A sufficient amount of ammonia was added to adjust the pH of the mixture to about 8.0, at which time a large quantity of a grey precipitate appeared. The precipitate was recovered utilizing a Buchner funnel, was washed with distilled water until the wash water was neutral and was air dried in an oven at 90° to 110°C. Approximately 30 gms of 3,5-dimethyl-1-(3-hydroxyphenyl) pyrazole were recovered.

EXAMPLE III 24.4 gms (0.13 moles) of 3.5-dimethyl-1-(3-hydroxyphenyl) pyrazole produced in accordance with Example II and 27.0 gms (0.095 moles) of o-(4-diethylamino-2-hydroxy benzoyl) benzoic acid were dissolved in 400 ml of concentrated $H_2SO_4$ maintained at a temperature of 0° to 10°C. Thereafter, the temperature of the mixture was raised to room temperature and the reaction was permitted to proceed for approximately 72 hrs. The reaction mixture was then poured into 1,500 ml of ice water and a sufficient amount of a 50% NaOH solution was added to make the overall mixture strongly alkaline (pH of 10–12). During this period ice was added as required to maintain the temperature below room temperature. The precipitated solids were extracted with benzene (3 × 800 ml), treated with activated carbon (Darco) and filtered. Thereafter the benzene was removed by evaporation to obtain 23 gms (approximately 52 percent yield) of 3'-diethylamino-6'-(3,5-dimethylpyrazol-1-yl)fluoran.

1.00 gms of this product were admixed with 20.0 gms of R-300 solvent (a commercial product of Kureha Corporation of America which is a mixture of isomeric diisopropyl naphthalenes and which is generally disclosed in U.S. Pat. No. 3,806,463 to Konishi et al.) and this admixture was warmed slightly on a hot plate until a clear solution (solution A) was obtained. Thereafter solution A was allowed to cool to room temperature. (When a small quantity of solution A was applied to an acidic clay coating on a paper substrate, a vivid red color appeared.) Then, 3.26 gms of terephthaloyl chloride were added to 10.0 gms of R-300 solvent and this mixture was also warmed slightly on a hot plate until a clear solution (solution B) was obtained. Solution B was then allowed to cool to room temperature. After solutions A and B were prepared, 100 gms of an aqueous solution containing 2.0 weight percent Elvanol 50-42 (a commercial product of E. I. duPont de Nemours which is a polyvinyl alcohol with 87 to 89% hydrolysis and a viscosity of 35 to 45 cps in a 4% aqueous solution at 20°C) were placed in a semi-micro Waring blender and then solutions A and B were mixed together at room temperature and the resultant solution was added to the Elvanol solution in the blender. The blender was activated and high shear agitation was continued for about 2 minutes until an emulsion having a dispersed phase particle size of about 2 to 10 microns was obtained. In this emulsion, the aqueous solution containing the Elvanol polyvinyl alcohol formed the continuous phase and the solution containing the R-300 solvent, 3'-diethyl-amino-6'-(3,5-dimethyl-pyrazol-1-yl)fluoran and terephthaloyl chloride formed the dispersed phase. The emulsion was then transferred to a suitable container such as a beaker and was stirred with a variable speed mechanical stirrer at 300 to 500 rpm while an aqueous solution containing 1.86 gms of diethylenetriamine, 1.44 gms of sodium carbonate and 20 ml of water was added. Stirring was continued at room temperature for about 24 hours until a stable pH of about 8.0 was observed. At this time, the particles of dispersed phase had become individually encapsulated in a polyamide shell. The slurry containing the microcapsules, and having the Elvanol polyvinyl alcohol binder in the continuous phase, was then drawn down on a 13 pound neutral base continuous bond paper sheet at a coating weight of approximately 2.34 to 3.04 gms per square meter and the coated sheet was oven dried at a temperature of 110°C for about 30 to 45 seconds. The dry coating on the paper sheet was white. The dry coating of microcapsules containing 3'-diethylamino-6'-(3,5-dimethylpyrazol-1-yl)fluoran was then brought into contact with an acid-leached bentonite-type clay coating on the surface of another sheet of paper and when an impression was made on the reverse side of the sheet coated with microcapsules, a corresponding red colored reproduction of such impression immediately appeared on the acid-leached bentonite-type clay coating.

While the foregoing Example specifically discloses the production and use of 3'-diethylamino-6'-(3,5-dimethyl-pyrazol-1-yl)fluoran, it is pointed out that the present invention contemplates and specifically encompasses the similar production and use of 3'-amino-6' or 7'-(pyrazol-1-yl)fluoran compounds as disclosed above wherein the amino nitrogen atom carries either hydrogen atoms, methyl groups, ethyl groups, propyl groups, butyl groups, pentyl groups or any mixture of two of the foregoing and wherein the pyrazolyl group carries, at each of its 3 and 5 positions, either a hydrogen atom, a substituted or unsubstituted lower alkyl group having from one to five carbon atoms or a substituted or unsubstituted phenyl group.

Moreover, other solvents for color precursors are known to those skilled in the art to which this invention pertains and any solvent for 3'-amino-6' or 7'-(pyrazol-1-yl)fluoran compounds which does not substantially interfere with the formation of color when the compound is contacted with a co-reactant may be utilized. Specifically, it should be noted that dibutyl phthalate may be utilized as a solvent for the color precursors of the present invention. It should be appreciated that the compounds of the present invention are useful generally in the production and generation of colored marks and it is not critical to the present invention that the same be utilized in a copying system or in a microencapsulated form.

I claim:

1. In a pressure-sensitive recording system comprising a layer containing a substantially colorless color precursor compound and a layer of an electron-acceptor material, the improvement which comprises utilizing, as said color precursor compound, a chromogenic 3'-amino-(pyrazol-1-yl) fluoran compound having the following structural formula:

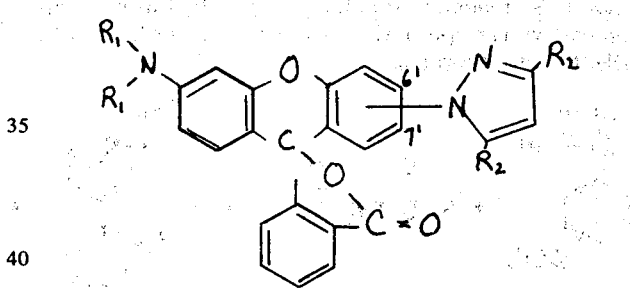

wherein each $R_1$ represents either a hydrogen atom or a lower alkyl group having from one to five carbon atoms; wherein each $R_2$ represents either a hydrogen atom, a lower alkyl group having from one to five carbon atoms or a phenyl group; and wherein the pyrazol group is attached to the fluoran moiety at either the 6' position or the 7' position of the latter.

2. The invention of claim 1 wherein said layer comprises microcapsules which contain said substantially colorless color precursor compound.

3. A pressure-sensitive recording system as set forth in claim 2 wherein 3'-diethylamino-6'-(3,5-dimethyl-pyrazol-1-yl)fluoran is utilized as said color precursor compound.

4. A pressure-sensitive recording system as set forth in claim 1 wherein 3'-diethylamino-6'-(3,5-dimethyl-pyrazol-1-yl)fluoran is utilized as said color precursor compound.

* * * * *